Feb. 16, 1971 J. V. PANCHO Plant Pat. 3,029
BOUGAINVILLEA PLANT
Filed Oct. 4, 1968
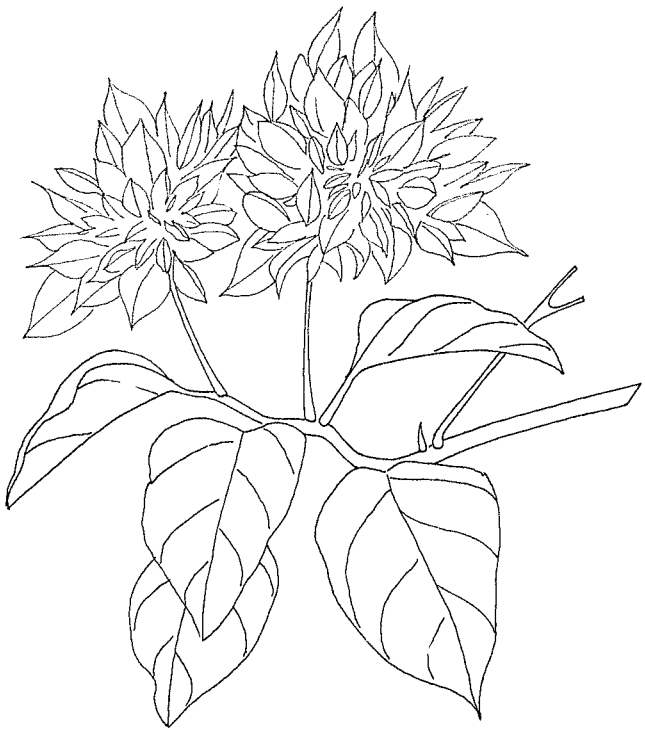
Inventor.
Juan V. Pancho
By: Robb & Robb
Attorneys.

United States Patent Office

Plant Pat. 3,029
Patented Feb. 16, 1971

3,029
BOUGAINVILLEA PLANT

Juan V. Pancho, College, Laguna, Philippines, assignor of one-half to David Barry, Jr., Honolulu, Hawaii Filed Oct. 4, 1968, Ser. No. 765,271
Int. Cl. A01h 5/00
U.S. Cl. Plt.—54 1 Claim The present invention relates to a new and distinct variety of Bougainvillea plant which was discovered by me as a sport in my cultivated garden located at College, Laguna, Philippines.

At the time of my discovery aforesaid, I was growing in my garden plants of the Bougainvillea variety known as "Pink Beauty" (unpatented). In the course of caring for these plants, I severely pruned the same, and as the plants continued to grow, my attention was attracted to one particular plant among the regular plantings of "Pink Beauty" which appeared to be quite different from all the other plants of "Pink Beauty." On close inspection of this particular plant, I found that it had sported, and I thereupon carefully preserved the sport, kept it under close observation, and in due course, I asexually reproduced the same by cuttings taken from the sport and grown by me in my garden aforementioned. Continued observations of the sport and the progeny thereof derived from the cuttings aforesaid, have convinced me that it comes true and is established through succeeding propagations and is a new variety which is distinguished from its parent, as well as from all other Bougainvillea varieties of which I am aware, as evidenced by the following unique combination of characteristics which are outstanding therein:

(1) Multiple bracts borne on arching stems (arching not seen in drawing) in sets of three upon three upon three, ranging up to 36 bracts, with each set of bracts arising in lieu of flowers where a flower would normally be produced and diminishing in size through each tripling from about 1½ inches in diameter to about 1/16 inch in diameter, giving a tufted appearance to the bract cluster and appearing from a distance like clustered roses;

(2) A distinctive and attractive Light Mallow Purple (Ridgway) bract color, generally corresponding to a soft light pink color, as depicted in the accompanying drawing.

Since my new Bougainvillea variety is otherwise generally similar to its parent variety "Pink Beauty," which is well known, no further detailed description thereof is necessary. While my new variety also bears some resemblance to the Bougainvillea variety known as "Carmencita" (U.S. Plant Pat. No. 2,514), the bract structure of the new variety is more arching and graceful, and the bract color of the new variety is substantial lighter and is unique in Bougainvillea cultivars and has a distinct and pleasing appeal to those who are inclined to favor pastel or soft colors.

While there is some resemblance between my new sport and the variety known as "Manila Red" which is the subject of U.S. Plant Pat. No. 2,630, its soft light pastel pink bract color is definitely distinct from that of "Manila Red" which is a much darker and stronger red color. Although the bract count of my new sport is quite variable and ranges up to 36 bracts, with an average number being closer to 20, the bracts are consistently more numerous than those of "Manila Red" which rarely exceeds 12 bracts and averages nearer to 10 bracts and are borne on erect stems, as grown under identical conditions in Southern California.

I claim:

1. A new and distincti variety of Bougainvillea plant, substantially as herein shown and described, characterized particularly as to novelty by the unique combination of multiple bracts borne on arching stems in sets of three upon three upon three, ranging up to 36 bracts, with each set of bracts arising in lieu of flowers where a flower would normally be produced and diminishing in size through each tripling from about 1½ inches in diameter to about 1/16 inch in diameter, giving a tufted appearance to the bract cluster and appearing from a distance like clustered roses, and a distinctive and attractive Light Mallow Purple (Ridgway) bract color, generally corresponding to a soft light pink color, as depicted in the accompanying drawing.

References Cited

UNITED STATES PATENTS

P.P. 2,630 5/1966 Barry ---------- 54

ROBERT E. BAGWILL, Primary Examiner